United States Patent
Lathrop et al.

(10) Patent No.: US 10,111,956 B2
(45) Date of Patent: Oct. 30, 2018

(54) CORTICOSTEROID COMPOSITIONS

(71) Applicant: TOLMAR, Inc., Fort Collins, CO (US)

(72) Inventors: Robert Lathrop, Fort Collins, CO (US); David Wade Osborne, Fort Collins, CO (US)

(73) Assignee: Tolmar, Inc., Fort Collins, CO (US)

( * ) Notice: Subject to any disclaimer, the term of this patent is extended or adjusted under 35 U.S.C. 154(b) by 0 days.

(21) Appl. No.: 14/294,764

(22) Filed: Jun. 3, 2014

(65) Prior Publication Data

US 2014/0357607 A1 Dec. 4, 2014
US 2015/0209429 A9 Jul. 30, 2015

Related U.S. Application Data

(63) Continuation of application No. PCT/US2014/040560, filed on Jun. 2, 2014.

(60) Provisional application No. 61/830,531, filed on Jun. 3, 2013.

(51) Int. Cl.

| | |
|---|---|
| *A61K 31/58* | (2006.01) |
| *A61K 31/573* | (2006.01) |
| *A61K 47/14* | (2017.01) |
| *A61K 9/06* | (2006.01) |
| *A61K 31/567* | (2006.01) |
| *A61K 9/00* | (2006.01) |
| *A61K 47/10* | (2017.01) |
| *A61K 9/107* | (2006.01) |
| *A61K 31/56* | (2006.01) |

(52) U.S. Cl.
CPC ............ *A61K 47/14* (2013.01); *A61K 9/0014* (2013.01); *A61K 9/06* (2013.01); *A61K 9/107* (2013.01); *A61K 31/56* (2013.01); *A61K 31/567* (2013.01); *A61K 31/573* (2013.01); *A61K 31/58* (2013.01); *A61K 47/10* (2013.01)

(58) Field of Classification Search
CPC ...... A61K 31/58; A61K 31/573; A61K 47/14; A61K 9/06; A61K 9/0014
See application file for complete search history.

(56) References Cited

U.S. PATENT DOCUMENTS

| | | |
|---|---|---|
| 4,305,936 A | 12/1981 | Klein |
| 4,863,738 A | 9/1989 | Taskovich |
| 5,728,690 A * | 3/1998 | Chen .................... A61K 9/0014 424/78.05 |
| 5,756,014 A | 5/1998 | Mathur |
| 5,824,666 A | 10/1998 | Deckner et al. |
| 5,840,719 A | 11/1998 | Rubin et al. |

(Continued)

FOREIGN PATENT DOCUMENTS

| | | |
|---|---|---|
| CN | 102940594 A | 2/2013 |
| EP | 1163902 A2 | 12/2001 |

(Continued)

OTHER PUBLICATIONS

Hydrocortisone 2.5% Cream; http://www.drugs.com/pro/hydrocortisone-2-5.html ; accessed Jun. 5, 2015.*

(Continued)

*Primary Examiner* — Timothy P Thomas
(74) *Attorney, Agent, or Firm* — Sheridan Ross P.C.

(57) ABSTRACT

The present disclosure generally relates to pharmaceutical corticosteroid compositions, and methods of making the same.

22 Claims, 2 Drawing Sheets

(56) References Cited

U.S. PATENT DOCUMENTS

| | | |
|---|---|---|
| 5,874,074 A | 2/1999 | Smith |
| 5,948,416 A | 9/1999 | Wagner et al. |
| 5,972,920 A | 10/1999 | Seidel |
| 5,989,536 A | 11/1999 | Deckner et al. |
| 6,066,292 A | 5/2000 | Purwar |
| 6,113,921 A | 9/2000 | Friedman et al. |
| 6,126,920 A | 10/2000 | Jones et al. |
| 6,300,326 B1 | 10/2001 | Dobbs et al. |
| 6,512,010 B1 | 1/2003 | Gale et al. |
| 6,723,714 B2 | 4/2004 | Hanna |
| 6,777,401 B2 | 8/2004 | Hanna |
| 6,843,983 B2 | 1/2005 | Bright-Ellington |
| 7,078,055 B2 | 7/2006 | Sessions et al. |
| 7,186,416 B2 | 3/2007 | Popp et al. |
| 7,217,422 B2 | 5/2007 | Gans et al. |
| 7,220,424 B2 | 5/2007 | Gans et al. |
| 7,378,405 B2 | 5/2008 | Patel |
| 7,666,859 B2 | 2/2010 | Turkowitz |
| 7,700,076 B2 | 4/2010 | Tamarkin et al. |
| 7,704,518 B2 | 4/2010 | Tamarkin et al. |
| 7,771,733 B2 | 8/2010 | Gans et al. |
| 7,794,738 B2 | 9/2010 | Gans et al. |
| 7,820,145 B2 | 10/2010 | Tamarkin et al. |
| 8,114,385 B2 | 2/2012 | Tamarkin et al. |
| 8,187,640 B2 | 5/2012 | Dunn |
| 8,232,264 B2 | 7/2012 | Gans et al. |
| 8,372,825 B2 | 2/2013 | Turkowitz |
| 8,389,502 B2 | 3/2013 | Patel |
| 8,580,286 B2 | 11/2013 | Pearlman |
| 8,617,578 B2 | 12/2013 | Fares et al. |
| 8,647,671 B2 | 2/2014 | Pearlman |
| 8,703,105 B2 | 4/2014 | Tamarkin et al. |
| 8,809,307 B2 | 8/2014 | Angel et al. |
| 2004/0180870 A1 | 9/2004 | Hanna |
| 2004/0198709 A1 | 10/2004 | Gans et al. |
| 2006/0140984 A1 | 6/2006 | Tamarkin et al. |
| 2006/0229364 A1 | 10/2006 | Hobbs et al. |
| 2007/0027152 A1 | 2/2007 | Clark et al. |
| 2007/0264344 A1 | 11/2007 | Segura-Orsoni et al. |
| 2007/0292359 A1 | 12/2007 | Friedman et al. |
| 2007/0292461 A1 | 12/2007 | Tamarkin et al. |
| 2008/0031907 A1 | 2/2008 | Tamarkin et al. |
| 2008/0044444 A1 | 2/2008 | Tamarkin et al. |
| 2008/0063607 A1 | 3/2008 | Tamarkin et al. |
| 2008/0064672 A1 | 3/2008 | Fares et al. |
| 2008/0138293 A1 | 6/2008 | Tamarkin et al. |
| 2008/0206161 A1 | 8/2008 | Tamarkin et al. |
| 2009/0088413 A1 | 4/2009 | Burkenstock, Sr. |
| 2009/0233892 A1 | 9/2009 | Sen et al. |
| 2009/0239835 A1 | 9/2009 | Daube et al. |
| 2011/0033402 A1 | 2/2011 | Modi |
| 2011/0059985 A1 | 3/2011 | Schmidts et al. |
| 2011/0269726 A1 | 11/2011 | Goldburt |
| 2011/0308985 A1 | 12/2011 | Van Bogaert |
| 2012/0022019 A1 | 1/2012 | Sulur et al. |
| 2012/0040927 A1 | 2/2012 | Sulur et al. |
| 2012/0115828 A1 | 5/2012 | Sulur et al. |
| 2012/0270835 A1 | 10/2012 | Sulur et al. |
| 2013/0123221 A1 | 5/2013 | Pearlman |
| 2014/0024629 A1 | 1/2014 | Pearlman |
| 2014/0179649 A1 | 6/2014 | Pearlman |
| 2014/0219929 A1 | 8/2014 | Tamarkin et al. |
| 2014/0227204 A1 | 8/2014 | Turkowitz |
| 2014/0234227 A1 | 8/2014 | Yelin et al. |
| 2014/0243299 A1 | 8/2014 | Gurge et al. |

FOREIGN PATENT DOCUMENTS

| | | | |
|---|---|---|---|
| GB | 1048820 | 12/1966 | |
| WO | 98/10770 | 3/1998 | |
| WO | 00/00181 | 1/2000 | |
| WO | 2005/102287 A2 | 11/2005 | |
| WO | WO 2006099374 A1 * | 9/2006 | ........... A61K 31/045 |
| WO | 2008/081175 A2 | 7/2008 | |
| WO | 2011/154004 A1 | 12/2011 | |
| WO | WO 2011154004 A1 * | 12/2011 | |
| WO | 2013/076160 A1 | 5/2013 | |
| WO | WO 2014126370 A1 * | 8/2014 | ........... A61K 31/722 |

OTHER PUBLICATIONS

Wayback machine capture of Hydrocortisone 2.5% Cream webpage; https://web.archive.org/web/20120417075602/http://www.drugs.com/pro/hydrocortisone-2-5.html; accessed Jun. 5, 2015.*

Osborne, "Review of Changes in Topical Drug Product Classification," Pharmaceutical Technology, 2008, vol. 32, Issue 10, pp. 66-74, retrieved from internet on Sep. 10, 2014, <http://license.icopyright.net/user/viewFreeUse.act?fuid=MTg0NDk2Nzl%3D>.

Buhse et al., "Topical drug classification," International Journal of Pharmaceutics, 2005, vol. 295, pp. 101-112.

* cited by examiner

CORTICOSTEROID COMPOSITIONS

CROSS-REFERENCE TO RELATED APPLICATION

The present application is a continuation of International Patent Application No. PCT/US14/40560, which was filed with the U.S. Receiving Office on Jun. 2, 2014, and is entitled Corticosteroid Compositions. The present application claims priority to U.S. Provisional Patent Application No. 61/830,531, which was filed on Jun. 3, 2013, and is entitled Corticosteroid Compositions. The contents of the above-mentioned patent applications are hereby incorporated by reference in their entirety.

TECHNICAL FIELD

The present disclosure relates to pharmaceutical corticosteroid compositions, and methods of making the same.

BACKGROUND

Corticosteroids have limited solubility in many pharmaceutically acceptable solvents and are often prepared as suspensions at concentrations above their solubility limits. Suspending a steroid in a topical product can reduce bioavailability and, upon storage, lead to changes in suspended drug particle size, which in turn can cause highly variable bioavailability. Thus, pharmaceutically suitable solvents and systems having improved dissolution of topical steroids and/or that can completely dissolve steroids at typical commercial product concentration levels are needed.

The information included in this Background section of the specification is included for technical reference purposes only and is not to be regarded as subject matter by which the scope of the invention as defined in the claims is to be bound.

SUMMARY

The present disclosure is directed to pharmaceutical compositions comprising at least one fatty acid ester and at least one corticosteroid. The fatty acid ester is a propylene glycol monoester or diester such as propylene glycol monocaprylate or propylene glycol monolaurate, or a glyceryl monoester or a diester. The pharmaceutical composition can also include a solvent such as diethylene glycol monoethyl ether, hexylene glycol, propylene glycol, or water.

A method of making a pharmaceutical composition includes dissolving at least one corticosteroid in at least one fatty acid ester.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

DETAILED DESCRIPTION

The present disclosure provides pharmaceutical corticosteroid compositions and methods of making the same. The pharmaceutical compositions comprise corticosteroids and fatty acid esters. In certain aspects, the fatty acid esters, optionally in combination with other components, dissolve corticosteroids at surprisingly high concentrations compared to previously known solvents, compositions, and combinations. In various aspects, the solubility of corticosteroids unexpectedly increases when they are combined with fatty acid esters and optionally other components.

The compositions and methods allow for improved bioavailability, both in terms of increased bioavailability and more consistent delivered drug levels, more reliable processing, and reduction or elimination of drug particle ripening (i.e. growing particle size) upon storage, all as compared to known compositions and methods.

Corticosteroids

The presently disclosed pharmaceutical compositions comprise one or more corticosteroids.

Examples of corticosteroids include, but are not limited to, aclovate, alclometasone dipropionate, amcinafel, amcinafide, amcinonide, aristocort A, augmented betamethasone dipropionate, beclamethasone, beclopmethasone dipropionate, betamethasone, betamethasone benzoate, betamethasone-17-benzoate, betamethasone dipropionate, betamethasone sodium phosphate and acetate, betamethasone valerate, betamethasone-17-valerate, chloroprednisone, clobetasol propionate, clobetasone propionate, clocortelone, cordran, corticosterone, cortisol, cortisol acetate, cortisol cypionate, cortisol sodium phosphate, cortisol sodium succinate, cortisone, cortisone acetate, cortodoxone, cyclocort, deflazacort, defluprednate, descinolone, desonide, desowen, desoximetasone, desoxycorticosterone acetate, desoxycorticosterone pivalate, 11-desoxycortisol, dexamethasone, dexamethasone acetate, dexamethasone sodium phosphate, dichlorisone, diflorasone diacetate, dihydroxycortisone, diprolen, diprolene, diprosone, esters of betamethasone, florone, flucetonide, flucloronide, flucortolone, fludrocortisone, fludrocortisone acetate, flumethalone, flumethasone, flumethasone pivalate, flunisolide, fluocinolone acetonide, fluocinolone acetonide acetate, fluocinonide, fluorametholone, fluorocortisone, fluperolone, fluprednisolone, flurandrenolide, fluoroandrenolone acetonide, fluticasone propionate, fuprednisolone, halcinonide, halobetasol propionate, halog, hydrocortamate, hydrocortisone, hydrocortisone acetate, hydrocortisone butyrate, hydrocortisone valerate, hydrocortisone-17-valerate, kenalog, lidex, locold, locorten, maxiflor, medrysone, meprednisone, methylprednisolone, 6α-methylprednisolone, methylprednisolone acetate, methylprednisolone sodium succinate, methylprednisone, mometasone furoate, paramethasone, paramethasone acetate, prednidone, prednisone, prednisolone, prednisolone acetate, prednisolone sodium phosphate, prednisolone sodium succinate, prednisolone tebutate, prednisone, psorcon, synalar, temovate, tetrahydrocortisol, topicort, topicort LP, triamcinolone, triamcinolone acetonide, triamcinolone diacetate, triamcinolone hexacotonide, tridesilone, valisone, and westcort. It will be understood that any single corticosteroid can be used separately, or in combination with any other corticosteroid or corticosteroids.

In one aspect, the corticosteroid is betamethasone dipropionate. In another aspect, the corticosteroid is clobetasol propionate. In another aspect, the corticosteroid is fluticasone propionate. In still another aspect, the corticosteroid is hydrocortisone. In still another aspect, the corticosteroid is hydrocortisone butyrate. In yet another aspect, the corticosteroid is triamcinolone acetonide.

Fatty Acid Esters

The presently disclosed pharmaceutical compositions can comprise one or more fatty acid esters.

Fatty acid esters are produced from combinations of an alcohol and one or more fatty acids according to the following general formula (I):

(I)

A hydroxyl oxygen of the alcohol forms a bond with a carboxyl carbon of the fatty acid in a reaction that releases water and creates an ester bond between the alcohol and fatty acid.

The fatty acid of a fatty acid ester can be saturated or unsaturated. A saturated fatty acid of a fatty acid ester can include, but is not limited to, ethantic acid (7 carbon atoms), caprylic acid (8 carbon atoms), pelargonic acid (9 carbon atoms), capric acid (10 carbon atoms), undecylic acid (11 carbon atoms), lauric acid (12 carbon atoms), tridecylic acid (13 carbon atoms), and myristic acid (14 carbon atoms). An unsaturated fatty acid of a fatty acid ester can include, but is not limited to, palmitoleic acid (16:1($\Delta^9$)), oleic acid (18:1 ($\Delta^9$)), linoleic acid (18:2($\Delta^{9,12}$)), and linolenic acid (18:3 ($\Delta^{9,12,15}$)).

Fatty acid esters can be liquid or solid at room temperature. Their melting temperature is based at least in part on the carbon chain length and level of saturation of the component fatty acid or acids. The melting points of long-chain fatty acids and the corresponding fatty acid esters tend to decrease with the introduction of double bonds into the chain.

Propylene Glycol Esters

In one embodiment, a fatty acid ester is a propylene glycol ester.

Propylene glycol esters are esters produced from combinations of propylene glycol and one fatty acid (a propylene glycol monoester) or two fatty acids (a propylene glycol diester). The fatty acid moieties in a propylene glycol diester can be the same or different. In a propylene glycol monoester, a fatty acid substituted at one hydroxyl group of propylene glycol creates one ester linkage, as shown in the following formula (III). In a propylene glycol diester, two fatty acids substituted at both hydroxyl groups of propylene glycol create two ester linkages, as shown in the following formula (IV):

(III)

(IV)

The fatty acid moieties in a propylene glycol ester include, but are not limited to, enthantic acid, caprylic acid, pelargonic acid, capric acid, undecylic acid, lauric acid, tridecylic acid, myristic acid, palmitoleic acid, oleic acid, linoleic acid, and linolenic acid.

Examples of propylene glycol monoesteres include, but are not limited to, propylene glycol monoenthantate, propylene glycol monocaprylate, propylene glycol monopelargonate, propylene glycol monocaprate, propylene glycol monoundecylate, propylene glycol monolaurate, propylene glycol monotridecylate, propylene glycol monomyristate, propylene glycol monopalmitolate, propylene glycol monolate, propylene glycol monolinolate, and propylene glycol monolinolenate.

Examples of propylene glycol diesters include, but are not limited to, propylene glycol dienthantate, propylene glycol dicaprylate, propylene glycol dipelargonate, propylene glycol dicaprate, propylene glycol diundecylate, propylene glycol dilaurate, propylene glycol ditridecylate, propylene glycol dimyristate, propylene glycol dipalmitolate, propylene glycol dioolate, propylene glycol dilinolate, and propylene glycol dilinolenate. Other examples of propylene glycol diesters include a diester of any two different fatty acids such as propylene glycol diester of caprylic acid and capric acid, a propylene glycol diester of caprylic acid and lauric acid, and a propylene glycol diester of capric acid and lauric acids.

In one embodiment, a propylene glycol ester is propylene glycol monocaprylate. In another embodiment, a propylene glycol ester is propylene glycol monolaurate.

Commercially available propylene glycol fatty acid esters include, but are not limited to, propylene glycol monocaprylate (Capmul 908P, Capmul PG-8 NF, Abitec), propylene glycol dicaprylate (Nikkol Sefsol 228, Nikko), propylene glycol dipelargonate, propylene glycol caprylate caprate (LABRAFAC PG, Gattefosse), propylene glycol dicaprate (Captex 100, Abitec), propylene glycol dicaprylate dicaprate (Captex 200, Abitec), propylene glycol monolaurate (Capmul PG-12 EP/NF, Abitec), propylene glycol dilaurate (Capmul PG-2L EP/NF, Abitec), and propylene glycol myristate.

Glyceryl Esters

In one embodiment, a fatty acid ester is a glyceryl ester.

Glyceryl esters are esters produced from combinations of glycerol and one fatty acid (a glyceryl monoester, or monoacylglycerol), two fatty acids (a glyceryl diester, or diacylglycerol), or three fatty acids (a glyceryl triester, or triacylglycerol). The fatty acids moieties in a glyceryl diester or triester can be the same or different. A fatty acid substituted at one hydroxyl group of glycerol creates one ester linkage, as shown in formula (VI) below. Fatty acids substituted at two hydroxyl groups of glycerol create two ester linkages, as shown in the following formula (VII), and fatty acids substituted at the three hydroxyl groups of glycerol create three ester linkages, as shown in the following formula (VIII):

The fatty acid moieties in a glyceryl ester include, but are not limited to, ethantic acid, caprylic acid, pelargonic acid, capric acid, undecylic acid, lauric acid, tridecylic acid, myristic acid, palmitoleic acid, oleic acid, linoleic acid, and linolenic acid.

Examples of glyceryl monoesters include, but are not limited to, glyceryl monoethantate, glyceryl monocaprylate, glyceryl monopelargonate, glyceryl monocaprate, glyceryl monoundecylate, glyceryl monolaurate, glyceryl monotridecylate, glyceryl monomyristate, glyceryl monopalmitolate, glyceryl monoolate, glyceryl monolinolate, and glyceryl monolinolenate.

Examples of glyceryl diesters include, but are not limited to, glyceryl dienthantate, glyceryl dicaprylate, glyceryl dipelargonate, glyceryl dicaprate, glyceryl diundecylate, glyceryl dilaurate, glyceryl ditridecylate, glyceryl dimyristate, glyceryl dipalmitolate, glyceryl dioolate, glyceryl dilinolate, and glyceryl dilinolenate. Other examples of glyceryl diesters include a diester of any two different fatty acids such as a glyceryl diester of caprylic acid and capric acid, a glyceryl diester of caprylic acid and lauric acid, and a glyceryl diester of capric acid and lauric acids.

Examples of glyceryl triesters include, but are not limited to, glyceryl trienthantate, glyceryl tricaprylate, glyceryl tripelargonate, glyceryl tricaprate, glyceryl triundecylate, glyceryl trilaurate, glyceryl tritridecylate, glyceryl trimyristate, glyceryl tripalmitolate, glyceryl trioolate, glyceryl trilinolate, glyceryl trilinolenate. Other examples of glyceryl triesters include a trimester of any combination of fatty acids such as a glyceryl triester of caprylic acid, capric acid and lauric acid.

Commercially available glyceryl fatty acid esters include, but are not limited to, glyceryl monocaprylate (Capmul 708G, Capmul MCM C8, Capmul MCM C8 EP, Abitec), glyceryl monocaprate (Capmul MCM C10, Abitec), and glyceryl caprylate/caprate (Capmul MCM NF, Campul MCM EP, Abitec).

Composition Solvent Components

A pharmaceutical composition can comprise one or more components that can serve as corticosteroid solvents. In one embodiment, a fatty acid ester, optionally in combination with one or more additional fatty acid esters, serves as a corticosteroid solvent. In another embodiment, a fatty acid ester, optionally in combination with one or more pharmaceutically acceptable solvents, serves as corticosteroid solvent. In another embodiment, a fatty acid ester, optionally in combination with one or more additional fatty acid esters and one or more pharmaceutically acceptable solvents, serves as corticosteroid solvent.

A fatty acid ester in combination with one or more additional fatty acid esters includes, but is not limited to, two or more propylene glycol esters; two or more propylene glycol monoesters; two or more propylene glycol diesters; and one or more propylene glycol monoesters with one or more propylene glycol diesters.

Other fatty acid ester combinations include, but are not limited to, two or more glyceryl esters; two or more glyceryl monoesters; two or more glyceryl diesters; two or more glyceryl triesters; one or more glyceryl monoesters with one or more glyceryl diesters; one or more glyceryl diesters with one or more glyceryl triesters; one or more glyceryl monoesters with one or more glyceryl triesters; and one or more glyceryl monoesters with one or more glyceryl diesters and with one or more glyceryl triesters.

Further fatty acid ester combinations include, but are not limited to, propylene glycol monocaprylate and propylene glycol dicaprylate; propylene glycol monocaprylate and propylene glycol monocaprate; propylene glycol monocaprylate and propylene glycol dicaprate; propylene glycol monocaprylate and glyeryl monocaprylate; propylene glycol monocaprylate and glyceryl dicaprylate; propylene glycol monocaprylate and glyceryl monocaprate; propylene glycol monocaprylate and glyceryl dicaprate; propylene glycol monocaprylate and propylene glycol monolaurate; propylene glycol monocaprylate and propylene glycol dilaurate; propylene glycol monocaprylate and glyceryl monolaurate; propylene glycol monocaprylate and glyceryl dilaurate; propylene glycol dicaprylate and propylene glycol monocaprate; propylene glycol dicaprylate and propylene glycol dicaprate; propylene glycol dicaprylate and glyeryl monocaprylate; propylene glycol dicaprylate and glyeryl dicaprylate; propylene glycol dicaprylate and glyceryl monocaprate; propylene glycol dicaprylate and glyceryl dicaprate; propylene glycol dicaprylate and propylene glycol monolaurate; propylene glycol dicaprylate and propylene glycol dilaurate; propylene glycol dicaprylate and glyceryl monolaurate; and propylene glycol dicaprylate and glyceryl dilaurate.

Still further fatty acid ester combinations include, but are not limited to, propylene glycol monocaprate and propylene glycol dicaprylate; propylene glycol monocaprate and propylene glycol dicaprate; propylene glycol monocaprate and glyeryl monocaprylate; propylene glycol monocaprate and glyeryl dicaprylate; propylene glycol monocaprate and glyceryl monocaprate; propylene glycol monocaprate and glyceryl dicaprate; propylene glycol monocaprate and propylene glycol monolaurate; propylene glycol monocaprate and propylene glycol dilaurate; propylene glycol monocaprate and glyceryl monolaurate; propylene glycol monocaprate and glyceryl dilaurate; propylene glycol dicaprate and propylene glycol monocaprate; propylene glycol dicaprate and glyeryl monocaprylate; propylene glycol dicaprate and glyeryl dicaprylate; propylene glycol dicaprate and glyceryl monocaprate; propylene glycol dicaprate and glyceryl dicaprate; propylene glycol dicaprate and propylene glycol monolaurate; propylene glycol dicaprate and propylene glycol dilaurate; propylene glycol dicaprate and glyceryl monolaurate; and propylene glycol dicaprate and glyceryl dilaurate.

When a fatty acid ester is optionally combined with one or more pharmaceutically acceptable solvents, the one or more pharmaceutically acceptable solvents can be present in any combination. Examples of pharmaceutically acceptable solvents include, but are not limited to, alcohol, castor oil, 3-[(3-cholamidopropyl)dimethylammonio]-1-propane-sulfonate, cholesterol NF, cholic acid, citric acid, 3-cyclohexene-1-methanol, dehydrated alcohol, deoxycholic acid, diethylene glycol monoethyl ether, diisopropanolamine (1:9), diisopropyl adipate, α4-dimethyl-a-(4-methyl-3-pentenyl), ethoxydiglycol, ethoxylated alcohol, ethyl alcohol, ethylene glycol, fatty alcohol citrate, glycerin, 1-hexadecanol, 1,2,6-hexanetriol, hexylene glycol, hydroxypropyl beta-cyclodextrin, isopropyl alcohol, isopropyl myristate, isopropyl palmitate, lecithin, mineral oil, 2-methyl-1,3-propanediol, oleyl alcohol, phosphoric acid, polyethylene glycols, polyethylene glycol 300, polyethylene glycol 400, polyethylene glycol 1450, polyethylene glycol 7000, polyethylene glycol 8000, polyethylene glycol 1000 monocetyl ether, polyethylene glycol monostearate, polyoxyl 20 cetostearyl ether, polyoxypropylene 15-stearyl ether, polysorbates, polysorbate 20, polysorbate 40, polysorbate 60, polysorbate 80, potassium hydroxide, propylene carbonate, propylene glycol, propylethylene glycol 4, neopentyl alcohol, SD alcohol 40, sodium lauryl sulfate, sorbitan monostearate, sorbitan stearate, taurodeoxycholic acid, triacetin, triethylene glycol, trimethylene glycol, vitamin E, vitamin E acetate, and water.

In one embodiment, the one or more pharmaceutically acceptable solvents are selected from diethylene glycol monoethyl ether, hexylene glycol, propylene glycol, and water. In one embodiment, the pharmaceutically acceptable solvent is diethylene glycol monoethyl ether. In another embodiment, the pharmaceutically acceptable solvent is hexylene glycol. In another embodiment, the pharmaceutically acceptable solvent is propylene glycol. In another embodiment, the pharmaceutically acceptable solvent is water. In another embodiment, the one or more pharmaceutically acceptable solvents may be selected from benzyl alcohol, glycerin, dimethyl isosorbide, and propylene carbonate. In certain embodiments, the pharmaceutically acceptable solvent is benzyl alcohol. In certain embodiments, the pharmaceutically acceptable solvent is glycerin. In certain embodiments, the pharmaceutically acceptable solvent is isosorbide. In certain embodiments, the pharmaceutically acceptable solvent is propylene carbonate.

The one or more components that can serve as corticosteroid solvents can be used with any corticosteroid. The fatty acid esters that can serve as corticosteroid solvents can be used in any application for which a pharmaceutically acceptable solvent is used.

Solubility of Corticosteroids

A. Solubility in Fatty Acid Esters

Corticosteroids can partially or completely dissolve in the presently disclosed fatty acid esters. Corticosteroids can be soluble in a fatty acid ester at any percent (w/w). In one embodiment, a corticosteroid is soluble in a fatty acid ester at 0.25% w/w to 4.5% w/w. In one embodiment, a corticosteroid is soluble in a fatty acid ester at more than 0.25% w/w. In another embodiment, a corticosteroid can be soluble at more than 0.50% w/w. In another embodiment, a corticosteroid can be soluble at more than 0.75% w/w. In still another embodiment, a corticosteroid can be soluble at more than 1.0% w/w. In yet another embodiment, a corticosteroid can be soluble at more than 2.0% w/w. In a further embodiment, a corticosteroid can be soluble at more than 3.0% w/w. In a still further embodiment, a corticosteroid can be soluble at more than 4.0% w/w.

In one embodiment, a corticosteroid can be soluble in a fatty acid ester at less than 5.0% w/w. In another embodiment, a corticosteroid can be soluble at less than 4.0% w/w. In another embodiment, a corticosteroid can be soluble at less than 3.0% w/w. In still another embodiment, a corticosteroid can be soluble at less than 2.0% w/w. In yet another embodiment, a corticosteroid can be soluble at less than 1.0% w/w. In a further embodiment, a corticosteroid can be soluble at less than 0.75% w/w. In a still further embodiment, a corticosteroid can be soluble at less than 0.5% w/w.

It is unexpected that corticosteroids can be more soluble in a fatty acid ester than in a pharmaceutically acceptable solvent such as isopropyl myrsitate. As depicted in Table 1 and described in Example 1, examples of corticosteroids that are more soluble in a fatty acid ester, such as propylene glycol monocaprylate, than in a pharmaceutically acceptable solvent, such as isopropyl myrsitate, include, but are not limited to, betamethasone dipropionate, clobetasol propionate, fluticasone propionate, hydrocortisone, hydrocortisone butyrate, and triamcinolone acetonide.

A corticosteroid can be any number of times more soluble in a fatty acid ester than in a pharmaceutically acceptable solvent such as isopropyl myristate. In one embodiment, a corticosteroid is 5 or more times more soluble in a fatty acid ester than in isopropyl myristate. In another embodiment, a corticosteroid is 10 or more times more soluble in a fatty acid ester than in isopropyl myristate. In another embodiment, a corticosteroid is 15 or more times more soluble in a fatty acid ester than in isopropyl myristate. In yet another embodiment, a corticosteroid is 20 or more times more soluble in a fatty acid ester than in isopropyl myristate. In still another embodiment, a corticosteroid is 25 or more times more soluble in a fatty acid ester than in isopropyl myristate. In a further embodiment, a corticosteroid is 30 or more times more soluble in a fatty acid ester than in isopropyl myristate.

In one embodiment, a corticosteroid is 30 or fewer times more soluble in a fatty acid ester than in isopropyl myristate. In another embodiment, a corticosteroid is 25 or fewer times more soluble in a fatty acid ester than in isopropyl myristate. In another embodiment, a corticosteroid is 20 or fewer times more soluble in a fatty acid ester than in isopropyl myristate. In still another embodiment, a corticosteroid is 15 or fewer times more soluble in a fatty acid ester than in isopropyl myristate. In yet another embodiment, a corticosteroid is 10 or fewer times more soluble in a fatty acid ester than in isopropyl myristate.

Without being limited to any mechanism or mode of action, fatty acid esters can act as solvents for corticosteroids due to their water miscible and polar nature. Propylene glycol monoesters can act as solvents for corticosteroids due to the polar contribution of the free hydroxyl group on propylene glycol. The close proximity of the free hydroxyl group to the ester bond between the alcohol and the fatty acid can also contribute to the solvent properties of propylene glycol monoesters. Further, the ester bond alone can contribute to the solvent properties of any propylene glycol ester. Glyceryl diesters and glyceryl monoesters can act as solvents for corticosteroids due to the polar contribution of the one or two, respectively, free hydroxyl groups on glycerol. The close proximity of the free hydroxyl group or groups to the ester bond or bonds between the alcohol and the fatty acid can also contribute to the solvent properties of glyceryl monoesters and diesters. Further, the ester bonds alone can contribute to the solubilizing properties of any glyceryl ester.

B. Solubility in Solvent Components

Corticosteroids can partially or completely dissolve in composition components that can serve as corticosteroid solvents.

Each corticosteroid has a given solubility in a given solvent. When two or more solvents are combined, it is common and expected that the two solvents will act independently of each other. For example, it is common and expected that the solubility of a corticosteroid in a combination solvent consisting of two solvents in equal proportion will be approximately the average of the solubility in each solvent alone. When two or more solvents are combined, it is also common and expected that the poorer solvent will have a diluting or interfering effect on the solvent properties of the better solvent when the two solvents are combined. For example, it is common and expected that a corticosteroid will be less soluble in a combination solvent consisting of two solvents in equal proportion than the average of the solubility in each solvent alone.

Figure 1:
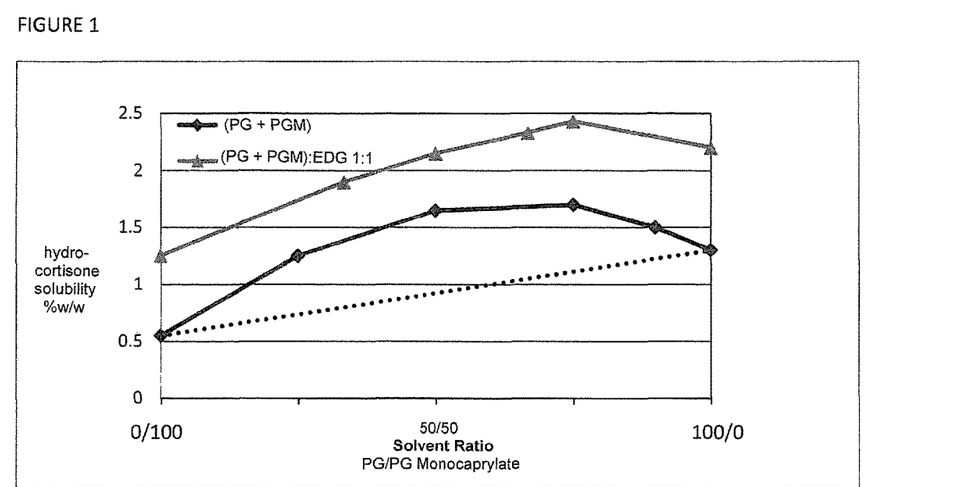
FIG. 1 depicts the solubility of hydrocortisone in mixtures of propylene glycol and propylene glycol monocaprylate, or of propylene glycol, propylene glycol monocaprylate, and ethoxydiglycol.

It is unexpected that a corticosteroid is more soluble in a mixture of solvent components than in each component alone. As depicted in FIG. 1 and described in Example 2, the solubility of hydrocortisone in each of a 50:50, 75:25, and 90:10 propylene glycol:propylene glycol monocaprylate solvent mixture is greater than in propylene glycol alone. The solubility of hydrocortisone in each of a 12:4:8, 12:6:6, 12:8:4, 12:9:3, and 12:12:0 ethoxydiglycol:propylene glycol:propylene glycol monocaprylate solvent mixture is greater than in propylene glycol alone. These results demonstrate the higher solubility of hydrocortisone in a combination of propylene glycol and propylene glycol monocaprylate; and in a combination of ethoxydiglycol, propylene glycol, and propylene glycol monocaprylate than expected.

Figure 2:
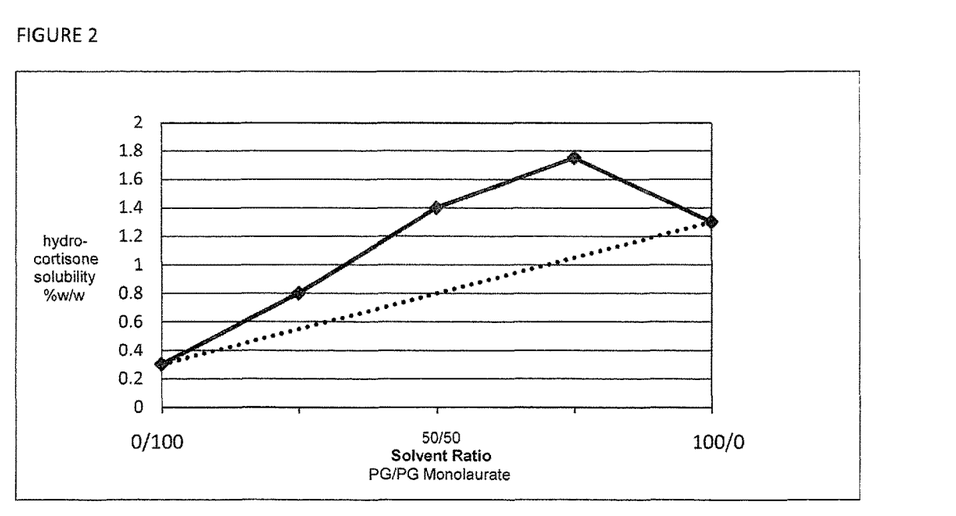
FIG. 2 depicts the solubility of hydrocortisone in mixtures of propylene glycol and propylene glycol monolaurate.

Further examples of the unexpected solubility of a corticosteroid in a mixture of solvent components are provided in FIG. 2 and Example 3. The solubility of hydrocortisone in both a 50:50 and a 75:25 propylene glycol:propylene glycol monolaurate solvent mixture were higher than in propylene glycol alone. These results demonstrate the higher solubility of hydrocortisone in a combination of propylene glycol and propylene glycol monolaurate than expected Still further examples of the unexpected solubility of a corticosteroid in a mixture of solvent components are provided in FIG. 4 and Example 5. The solubility of triamcinolone acetonide in each of a 25:75, 50:50, 75:25, and 90:10 propylene glycol:propylene glycol monocaprylate solvent mixture is greater than in propylene glycol alone. As additional examples, the solubility of hydrocortisone in each of a 12:3:9, 12:6:6, 12:9:3, and 12:12:0 ethoxydiglycol:propylene glycol:propylene glycol monocaprylate solvent mixture is greater than in propylene glycol alone. These results demonstrate the higher solubility of triamcinolone acetonide in a combination of propylene glycol and propylene glycol monocaprylate; and in a combination of ethoxydiglycol, propylene glycol, and propylene glycol monocaprylate than expected.

It is also unexpected that the solubility of a corticosteroid in a given solvent improves upon the addition of water to the solvent because water is known to be a poor corticosteroid solvent. As described in Example 6 and Table 8, the solubility of hydrocortisone in ethoxydiglycol with purified water is greater than in ethoxydiglycol alone. Hydrocortisone is also more soluble in propylene glycol monocaprylate with purified water than in propylene glycol monocaprylate alone. Hydrocortisone is also more soluble in an ethoxydiglycol:propylene glycol monocaprylate:propylene glycol solvent mixture with purified water than in the mixture alone.

A fatty acid ester can retain its solvent properties when combined with one or more pharmaceutically acceptable solvents in a mixture of solvent components. Combining a fatty acid ester with a pharmaceutically acceptable solvent can improve the corticosteroid solvent properties of the mixture compared to the pharmaceutically acceptable solvent alone. Combining a mixture of a fatty acid ester and a pharmaceutically acceptable solvent with another solvent, such as another pharmaceutically acceptable solvent, can further increase the solvent properties of the mixture compared to either or both of the pharmaceutically acceptable solvents alone. The pharmaceutically acceptable solvent can be diethylene glycol monoethyl ether, hexylene glycol, propylene glycol, or water.

A fatty acid ester can be compatible with any excipient in a formulation.

Formulations

The presently disclosed pharmaceutical compositions can be provided in a formulation. The formulation can be an injectable formulation. An injectable formulation can be a liquid that can be injected into the skin, underlying tissue, or any other area of the body. An injectable can be aqueous-based or solvent-based. An injectable can comprise dissolved polymers/copolymers or liquid polymers/copolymers such as polyglycolides, polylactides, and polycaprolactones, as described in U.S. Pat. No. 8,187,640, which is hereby expressly incorporated by reference in its entirety.

The formulation can be a topical formulation. For example, the topical formulation can be in the form of a liquid, an emulsion, a semisolid, or a colloidal dispersion, which are described in Osborne, *Pharmaceutical Technology* 32(10), 66-74 (2008), and Buhse et. al., *Int. J. Pharma.* 295, 101-112 (2005), which are hereby expressly incorporated by reference in their entirety. Examples of topical formulations include, but are not limited to, a cream, emulsion, foam, gel, liquid, lotion, mist, ointment, paste, shampoo, shampoo suspension, solution, spray, and suspension, which are described in Osborne, supra, and Buhse et. al., supra.

A topical formulation can be selected based on numerous factors including, but not limited to, the location to which the formulation will be applied, the condition to be treated, the desired corticosteroid potency, the desired corticosteroid penetration, and the desired hydration provided by the formulation.

In various aspects, the formulation is a cream. A cream can be a viscous liquid or semisolid emulsion, and can comprise greater than 20% water and volatiles and/or less than 50% hydrocarbons, waxes, or polyethylene glycol. A cream is either an oil-in-water cream with water as the continuous phase, or a water-in-oil cream with oil as the continuous phase. A cream can contain an emulsifier in addition to the oil phase and the water phase. The oil phase can be comprised of petrolatum and a fatty alcohol such as cetyl or stearyl alcohol. The aqueous phase can exceed the oil phase in volume and can comprise a humectant. The emulsifier can be a nonionic, anionic, cationic, or amphoteric surfactant. Various specific embodiments of creams comprising one or more fatty acid esters are described in Examples 7-10.

In various aspects, the formulation is a foam. A foam can be a dispersion of gas within a liquid or solid. A foam for topical application can be formed by packaging a pressurized gas with an emulsion; upon expulsion from the container the gas is trapped within the emulsion.

In various aspects, the formulation is a gel. A gel can be a semisolid solution or colloidal dispersion that can contain suspended particles. A gel can be solid at room temperature but melt on the skin. A gel can comprise an aqueous or alcoholic vehicle. A gel can also comprise a gelling agent, such as starch, cellulose derivatives, carbomers, magnesium-aluminum silicates, xanthan gum, colloidal silica, and aluminum or zinc soaps. The gelling agent can cross-link to form a gel-like structure, which can provide stiffness. Cross-linking can be pH-dependent. A gel can also comprise a dispersing agent such as alcohol or glycerin to help disperse components such as the gel-forming agent. Alternatively, or additionally, components can be dispersed by mechanical mixing or titration. Various specific embodiments of gels comprising one or more fatty acid esters are described in Examples 11 and 12.

In various aspects, the formulation is a lotion. A lotion can be a liquid emulsion comprising an aqueous vehicle and more than 50% water and volatiles. A lotion can exhibit Newtonian or pseudoplastic flow behavior. When rubbed onto the skin, a lotion can evaporate rapidly with a cooling sensation. A lotion can comprise an agent to help an active pharmaceutical agent remain in contact with the skin. Various specific embodiments of lotions comprising one or more fatty acid esters are described in Examples 11 and 12.

In various aspects, the formulation is an ointment. An ointment can be a semisolid suspension or emulsion, and can have a medium to high viscosity. An ointment can comprise less than 20% water and volatiles, and can comprise greater than 50% hydrocarbons, waxes, or polyethylene glycol. An ointment can be hydrating and an ointment can be occlusive. An ointment can not evaporate or be absorbed when rubbed onto the skin. An ointment can enhance the penetration of a corticosteroid into the skin. Various specific embodiments of ointments comprising one or more fatty acid esters are described in Examples 13 and 14.

In various aspects, the formulation is a paste. A paste can be a semisold that contains a large proportion (i.e., 20-50%) of solids finely dispersed in a fatty vehicle. A paste can adhere well to the skin and form a protective layer.

In various aspects, the formulation is a shampoo. A shampoo can be a liquid soap or detergent. A shampoo can be used to clean the hair and scalp, and can be used as a vehicle for a corticosteroid.

In various aspects, the formulation is a shampoo suspension. A shampoo suspension can be a liquid soap or detergent comprising one or more solid, insoluble substances dispersed in a liquid vehicle. A shampoo suspension can be used to clean the hair and scalp, and can be used as a vehicle for a corticosteroid.

In various aspects, the formulation is a solution. A solution can be a clear, homogeneous liquid molecular dispersion of at least one solute (solid, liquid, or gas) dissolved in a suitable vehicle. The vehicle can comprise one or more miscible liquids. A solution can comprise an aqueous component, an alcoholic component, and/or a gelling agent.

In various aspects, the formulation is a suspension. A suspension can be a two-phase liquid system comprising a solid suspended in an aqueous or alcoholic liquid vehicle.

Components of Formulations

A. Fatty Acid Esters

A formulation can comprise a fatty acid ester, as described above. In one embodiment, a formulation comprises a fatty acid ester at 1% w/w to 40% w/w. In another embodiment, a formulation comprises a fatty acid ester at 1% w/w to 30% w/w. In another embodiment, a formulation comprises a fatty acid ester at 2% w/w to 20% w/w. In yet another embodiment, a formulation comprises a fatty acid ester at 2% w/w to 12% w/w. In still another embodiment, a formulation comprises a fatty acid ester at 3% w/w to 12% w/w. In a further embodiment, a formulation comprises a fatty acid ester at 2% w/w to 10% w/w.

In one embodiment, a formulation comprises a fatty acid ester at more than 1% w/w. In another embodiment, a formulation comprises a fatty acid ester at more than 5% w/w. In another embodiment, a formulation comprises a fatty acid ester at more than 10% w/w. In yet another embodiment, a formulation comprises a fatty acid ester at more than 15% w/w. In still another embodiment, a formulation comprises a fatty acid ester at more than 20% w/w. In a further embodiment, a formulation comprises a fatty acid ester at more than 30% w/w.

In one embodiment, a formulation comprises a fatty acid ester at less than 40% w/w. In another embodiment, a formulation comprises a fatty acid ester at less than 30% w/w. In another embodiment, a formulation comprises a fatty acid ester at less than 20% w/w. In yet another embodiment, a formulation comprises a fatty acid ester at less than 15% w/w. In still another embodiment, a formulation comprises a fatty acid ester at less than 10% w/w. In a further embodiment, a formulation comprises a fatty acid ester at less than 5% w/w.

B. Pharmaceutically Acceptable Solvents

A formulation can comprise a pharmaceutically acceptable solvent, as described above. In one embodiment, a formulation comprises a pharmaceutically acceptable solvent at 1% w/w to 40% w/w. In another embodiment, a formulation comprises a pharmaceutically acceptable solvent at 1% w/w to 30% w/w. In another embodiment, a formulation comprises a pharmaceutically acceptable solvent at 2% w/w to 25% w/w. In yet another embodiment, a formulation comprises a pharmaceutically acceptable solvent at 3% w/w to 20% w/w. In still another embodiment, a formulation comprises a pharmaceutically acceptable solvent at 5% w/w to 12% w/w.

In one embodiment, a formulation comprises a pharmaceutically acceptable solvent at more than 1% w/w. In another embodiment, a formulation comprises a pharmaceutically acceptable solvent at more than 5% w/w. In another embodiment, a formulation comprises a pharmaceutically acceptable solvent at more than 10% w/w. In yet another embodiment, a formulation comprises a pharmaceutically acceptable solvent at more than 15% w/w. In still another embodiment, a formulation comprises a pharmaceutically acceptable solvent at more than 20% w/w. In a further embodiment, a formulation comprises a pharmaceutically acceptable solvent at more than 30% w/w.

In one embodiment, a formulation comprises a pharmaceutically acceptable solvent at less than 40% w/w. In another embodiment, a formulation comprises a pharmaceutically acceptable solvent at less than 30% w/w. In another embodiment, a formulation comprises a pharmaceutically acceptable solvent at less than 20% w/w. In yet another embodiment, a formulation comprises a pharmaceutically acceptable solvent at less than 15% w/w. In still another embodiment, a formulation comprises a pharmaceutically acceptable solvent at less than 10% w/w. In a further embodiment, a formulation comprises a pharmaceutically acceptable solvent at less than 5% w/w.

C. Mixtures of Solvent Components

A formulation can comprise more than one component that can serve as corticosteroid solvents, as described above.

The solvent components can be combined prior to being added to a formulation, or the components can be combined in the process of making the formulation.

Each component that can serve as a corticosteroid solvent can be present in any amount relative to another component. In one embodiment, the ratio (w:w) of one solvent component to another solvent component is 1:0. In another embodiment, the ratio (w:w) of one solvent component to another solvent component is from 1:0.1 to 1:5. In another embodiment, the ratio (w:w) of one solvent component to another solvent component is from 1:0.3 to 1:4. In still another embodiment, the ratio (w:w) of one solvent component to another solvent component is from 1:0.375 to 1:3.75.

In one embodiment, the ratio (w:w) of one solvent component to a combination of two other solvent components is from 1:0.5 to 1:7.5. In another embodiment, the ratio (w:w) of one solvent component to a combination of two other solvent components is from 1:1 to 1:6. In another embodiment, the ratio (w:w) of one solvent component to a combination of two other solvent components is from 1:1.5 to 1:5.5.

In one embodiment, a formulation comprises more than one component that can serve as corticosteroid solvents ("corticosteroid solvent mixture") at 2% w/w to 50% w/w. In another embodiment, a formulation comprises a corticosteroid solvent mixture at 3% w/w to 30% w/w. In another embodiment, a formulation comprises a corticosteroid solvent mixture at 3% w/w to 25% w/w. In yet another embodiment, a formulation comprises a corticosteroid solvent mixture at 3% w/w to 60% w/w. In still another embodiment, a formulation comprises a corticosteroid solvent mixture at 4% w/w to 40% w/w. In a further embodiment, a formulation comprises a corticosteroid solvent mixture at 5% w/w to 30% w/w.

In one embodiment, a formulation comprises a corticosteroid solvent mixture at more than 2% w/w. In another embodiment, a formulation comprises a corticosteroid solvent mixture at more than 5% w/w. In another embodiment, a formulation comprises a corticosteroid solvent mixture at more than 10% w/w. In yet another embodiment, a formulation comprises a corticosteroid solvent mixture at more than 20% w/w. In still another embodiment, a formulation comprises a corticosteroid solvent mixture at more than 30% w/w. In a further embodiment, a formulation comprises a corticosteroid solvent mixture at more than 40% w/w.

In one embodiment, a formulation comprises a corticosteroid solvent mixture at less than 60% w/w. In another embodiment, a formulation comprises a corticosteroid solvent mixture at less than 50% w/w. In another embodiment, a formulation comprises a corticosteroid solvent mixture at less than 40% w/w. In yet another embodiment, a formulation comprises a corticosteroid solvent mixture at less than 30% w/w. In still another embodiment, a formulation comprises a corticosteroid solvent mixture at less than 20% w/w. In a further embodiment, a formulation comprises a corticosteroid solvent mixture at less than 10% w/w.

Each component that can serve as a corticosteroid solvent can be present in any amount relative to another component. In one embodiment, the ratio (w:w) of one solvent component to another solvent component is 1:0. In another embodiment, the ratio (w:w) of one solvent component to another solvent component is from 1:0.1 to 1:5. In another embodiment, the ratio (w:w) of one solvent component to another solvent component is from 1:0.3 to 1:4. In still another embodiment, the ratio (w:w) of one solvent component to another solvent component is from 1:0.375 to 1:3.75.

In one embodiment, the ratio (w:w) of one solvent component to a combination of two other solvent components is from 1:0.5 to 1:7.5. In another embodiment, the ratio (w:w) of one solvent component to a combination of two other solvent components is from 1:1 to 1:6. In another embodiment, the ratio (w:w) of one solvent component to a combination of two other solvent components is from 1:1.5 to 1:5.5.

D. Corticosteroids

A formulation can also comprise one or more corticosteroids, as described above. In one embodiment, a formulation comprises one or more corticosteroids at 0.001% w/w to 5% w/w. In another embodiment, a formulation comprises one or more corticosteroids at 0.005% w/w to 3% w/w. In another embodiment, a formulation comprises one or more corticosteroids at 0.01% w/w to 2.5% w/w.

In one embodiment, a formulation comprises one or more corticosteroids at more than 0.001% w/w. In another embodiment, a formulation comprises one or more corticosteroids at more than 0.01% w/w. In another embodiment, a formulation comprises one or more corticosteroids at more than 0.05% w/w. In yet another embodiment, a formulation comprises one or more corticosteroids at more than 0.1% w/w. In still another embodiment, a formulation comprises one or more corticosteroids at more than 0.5% w/w. In a further embodiment, a formulation comprises one or more corticosteroids at more than 1% w/w.

In one embodiment, a formulation comprises one or more corticosteroids at less than 5% w/w. In another embodiment, a formulation comprises one or more corticosteroids at less than 3% w/w. In another embodiment, a formulation comprises one or more corticosteroids at less than 1% w/w. In yet another embodiment, a formulation comprises one or more corticosteroids at less than 0.5% w/w. In still another embodiment, a formulation comprises one or more corticosteroids at less than 0.1% w/w.

E. Penetration Enhancers

A topical formulation can comprise one or more penetration enhancers. In one embodiment, the one or more penetration enhancers enhance penetration of one or more corticosteroids through the skin. In another embodiment, the one or more penetration enhancers enhance penetration by reversibly decreasing the barrier resistance of the skin. In another embodiment, the one or more penetration enhancers enhance penetration by increasing the permeability of the stratum corneum.

Examples of suitable penetration enhancers include, but are not limited to, alcohols, alkanols, alkanones such as benzyl alcohol, decanol, ethanol, octanol, and propanol; amides and other nitrogenous compounds such as diethanolamine, dimethylacetamide, dimethylformamide, ethanolamine, 1-methyl-2-pyrrolidone, 2-pyrrolidone, triethanolamine, and urea; diisopropyl adipate; dimethyl isosorbide; ethers such as diethylene glycol monoethyl ether and diethylene glycol monomethyl ether; fatty acids such as lauric acid, oleic acid, and valeric acid; fatty acid esters such as ethyl oleate, isopropyl myristate, isopropyl palmitate, and methylpropionate; organic acids such as citric acid, salicylic acid, salicylates, and succinic acid; polyols and esters thereof such as butanediol, ethylene glycol, glycerol, 1,2,6 hexanetriol, polyethylene glycol, polyethylene glycol monolaurate, and propylene glycol; pyrrolidones such as 2-pyrrolidone; 1-substituted azacycloheptan-2-ones, such as 1-n-dodecylcyclazacycloheptan-2-one (laurocapram); sulphoxides such as decylmethylsulfoxide and dimethylsulphoxide; surfactants such as benzalkonium chloride, cetyltrimethylammonium bromide, lecithin, Poloxamer (231, 182, 184), sodium laurate, sodium lauryl sulfate, and Tween (20, 40, 60, 80); and terpenes.

F. Humectants

A topical formulation can comprise one or more humectants. In one embodiment, the one or more humectants are moistening agents that promote water retention due to their hygroscopic properties. In one embodiment, a humectant holds water against the skin so that the formulation does not dry out or dry down. Without being limited to any mechanism of mode of action, a humectant can improve solubility of a corticosteroid by promoting water retention because water can increase corticosteroid solubility. (Example 6.)

Examples of suitable humectants include, but are not limited to, ethylene glycol, fructose, glycerol, lactic acid, polyethylene glycol, propylene glycol, sorbitan, sorbitol, tetraethylene glycol, triethylene glycol, vitamin B, and any combination thereof.

One or more humectants can be present in a topical formulation at any acceptable amount. In one embodiment, a formulation comprises one or more humectants at 2% w/w to 25% w/w. In another embodiment, a formulation comprises one or more humectants at 8% w/w to 22% w/w. In another embodiment, a formulation comprises one or more humectants at 10% w/w to 14% w/w.

In one embodiment, a formulation comprises one or more humectants at more than 2% w/w. In another embodiment, a formulation comprises one or more humectants at more than 5% w/w. In another embodiment, a formulation comprises one or more humectants at more than 10% w/w. In yet another embodiment, a formulation comprises one or more humectants at more than 15% w/w. In still another embodiment, a formulation comprises one or more humectants at more than 20% w/w.

In one embodiment, a formulation comprises one or more humectants at less than 25% w/w. In another embodiment, a formulation comprises one or more humectants at less than 20% w/w. In another embodiment, a formulation comprises one or more humectants at less than 15% w/w. In yet another embodiment, a formulation comprises one or more humectants at less than 10% w/w. In still another embodiment, a formulation comprises one or more humectants at less than 5% w/w.

G. Emulsifiers

A formulation can comprise one or more emulsifiers. In one embodiment, the one or more emulsifiers are substances that promote the formation of an emulsion. In another embodiment, the one or more emulsifiers are substances that stabilize an emulsion.

Examples of suitable emulsifiers include, but are not limited to, carbomer copolymers, glyceryl mono and di-fatty acid esters, polyglycerin fatty acid esters, polyoxyethylene fatty acid esters, fatty alcohol ethoxylated ethers, sorbitan esters of fatty acids, sucrose esters of fatty acids, ethoxylated alkyl phenols, polyoxyethylene polyoxypropylene block polymers, polyoxypropylene polyoxyethylene ethers of fatty alcohols.

Methods of Use

Pharmaceutical compositions and/or corticosteroid formulation as disclosed herein can be used to treat any medical condition known in the art to be treated by corticosteroids. In some embodiments, pharmaceutical compositions and/or corticosteroid formulations disclosed herein can be used to decrease inflammation and/or to reduce the activity of the immune system in a variety of medical conditions. Medical conditions include, for example, atopic dermatitis, psoriasis, eczematous dermatitis, nummular dermatitis, irritant contact dermatitis, allergic contact dermatitis (such as poison ivy exposure, poison oak exposure, and poison sumac exposure), seborrheic dermatitis, stasis dermatitis, and other steroid responsive dermatoses. Corticosteroid formulation can also be used to treat, for example, acne vulgaris, alopecia, alopecia greata, vitiligo, eczema, xerotic eczema, keratosis pilaris, lichen planus, lichen sclerosus, lichen striatus, lichen simplex chronicus, prurigo nodularis, discoid lupus erythematosus, lymphocytic infiltrate of Jessner/Kanof, lymphacytoma cutis, pyoderma gangrenosum, pruritis ani, sarcoidosis, chondrodermatitis nodularis helices and other inflammatory dermatological disorders. Medical conditions can also include, for example, keloids, hypertrophic scars, pretibial myxedema and other infiltrative dermatological disorders. Additional medical conditions include, for example, granuloma annulare, necrobiosis lipoidica diabeticorum, sarcoidosis, and other noninfectious granulomas. Pharmaceutical compositions and/or corticosteroid formulations can also be used for their anti-pruritic and vasoconstriction properties.

EXAMPLES

The following examples illustrate various aspects of the disclosure, and should not be considered limiting.

Example 1—Solubility of Corticosteroids in Neat Solvents

The solubilities of various corticosteroids in propylene glycol (PG) monocaprylate, PG monolaurate, or isopropyl myristate were measured gravimetrically. Corticosteroid, PG monocaprylate, PG monolaurate, and/or isopropyl myristate were placed in glass vials and weighed on an analytical balance to four decimals places. Test solutions were stirred and shaken at room temperature for up to 30 minutes. Test solutions were examined at about 24 hours for clarity or non-dissolved material.

Solubility (% w/w) results are presented in Table 1. The results demonstrate that the highest percent solubility obtained with isopropyl myristate (0.25% w/w for clobetasol propionate) was lower than the lowest percent solubility obtained with either PG monocaprylate (0.3% w/w for fluticasone propionate) or PG monolaurate (0.3% w/w for each of hydrocortisone and triamcinolone acetonide).

TABLE 1

| Corticosteroid | PG Monocaprylate (% w/w) | PG Monolaurate (% w/w) | Isopropyl Myristate (% w/w) |
| --- | --- | --- | --- |
| Fluticasone Propionate | 0.3 | — | <0.03 |
| Hydrocortisone | 0.55 | 0.30 | <0.02 |
| Triamcinolone Acetonide | 0.65 | 0.30 | <0.04 |
| Mometasone Fuorate | 0.7 | — | — |
| Desonide | 1.15 | 0.40 | — |
| Hydrocortisone Butyrate | 2.0 | 1.35 | 0.10 |
| Betamethasone Dipropionate | 4.0 | 2.30 | 0.15 |
| Clobetasol Propionate | 4.0 | 1.80 | 0.25 |

The results also demonstrate that each tested corticosteroid was more soluble in PG monocaprylate than in isopropyl myristate. Fluticasone propionate was 10 times more soluble in PG monocaprylate than in isopropyl myristate. Hydrocortisone was at least 27 times more soluble in PG monocaprylate than in isopropyl myristate. Triamcinolone acetonide was at least 16 times more soluble in PG monocaprylate than in isopropyl myristate. Hydrocortisone butyrate was 20 times more soluble in PG monocaprylate than in isopropyl myristate. Betamethasone dipropionate was 27 times more soluble in PG monocaprylate than in isopropyl myristate. Clobetasol propionate was 16 times more soluble in PG monocaprylate than in isopropyl myristate.

Additionally, the results demonstrate that each tested corticosteroid was more soluble in PG monolaurate than in isopropyl myristate. Hydrocortisone was at least 15 times more soluble in PG monolaurate than in isopropyl myristate. Triamcinolone acetonide was at least 7.5 times more soluble in PG monolaurate than in isopropyl myristate. Hydrocortisone butyrate was 13.5 times more soluble in PG monolaurate than in isopropyl myristate. Betamethasone dipropionate was 15.3 times more soluble in PG monolaurate than in isopropyl myristate. Clobetasol propionate was 7.2 times more soluble in PG monolaurate than in isopropyl myristate.

Further, the results demonstrate that each corticosteroid was more soluble in PG monocapyrlate than in PG monolaurate. On average, a given corticosteroid was twice as soluble in PG monocapyrlate than in PG monolaurate.

Example 2—Solubility of Hydrocortisone in Mixtures of Components

A) Mixtures of PG and PG Monocaprylate

The solubility of hydrocortisone in mixtures of PG and PG monocaprylate was measured according to the procedure in Example 1.

Solubility (% w/w) results are presented in Table 2 and FIG. 1.

TABLE 2

| PG:PG Monocaprylate | Solubility (% w/w) |
| --- | --- |
| 100:0 | 1.30 |
| 90:10 | 1.50 |
| 75:25 | 1.70 |
| 50:50 | 1.65 |
| 25:75 | 1.25 |
| 0:100 | 0.55 |

In FIG. 1, the vertical axes indicate solubility (% w/w). The horizontal axis indicates the PG:PG monocaprylate ratio (w:w) in a given solvent mixture. The dashed solubility line indicates the expected solubility if each solvent (PG and PG monocaprylate) acted independently in a solvent mixture. The middle line (♦) depicts actual results of hydrocortisone solubility in a PG:PG monocaprylate solvent mixture. The upper line (▲) depicts actual results of hydrocortisone solubility in an ethoxydigycol:PG:PG monocaprylate solvent mixture.

FIG. 1 demonstrates that for each tested solvent mixture that contained both PG and PG monocaprylate (♦), hydrocortisone was more soluble in the mixture than expected (dashed line).

Solubility of hydrocortisone in a 50:50 PG:PG monocaprylate solvent mixture (1.65% w/w), a 75:25 PG:PG monocaprylate solvent mixture (1.70% w/w), and a 90:10 PG:PG monocaprylate solvent mixture (1.50% w/w) were all higher than in PG alone (i.e. 100:0 solvent mixture; 1.30% w/w). These results suggest a synergistic effect between PG and PG monocaprylate.

B) Effect of Addition of Ethoxydiglycol on Hydrocortisone Solubility in Mixtures of PG and PG Monocaprylate The solubility of hydrocortisone in mixtures of PG, PG monocaprylate, and ethoxydiglycol was measured according to the procedure in Example 1.

Solubility (% w/w) results are presented in Table 3 and FIG. 1.

TABLE 3

| Ethoxydiglycol:PG:PG Monocaprylate | Solubility (% w/w) |
| --- | --- |
| 12:12:0 | 2.20 |
| 12:9:3 | 2.43 |
| 12:8:4 | 2.33 |
| 12:6:6 | 2.17 |
| 12:4:8 | 1.90 |
| 12:0:12 | 1.25 |

FIG. 1 demonstrates that hydrocortisone was more soluble in a ethoxydiglycol:PG:PG monocaprylate solvent mixture (▲) than in a PG:PG monocaprylate solvent mixture (♦).

Solubility of hydrocortisone in a 12:4:8 ethoxydiglycol:PG:PG monocaprylate solvent mixture (1.90% w/w), a 12:6:6 ethoxydiglycol:PG:PG monocaprylate solvent mixture (2.17% w/w), a 12:8:4 ethoxydiglycol:PG:PG monocaprylate solvent mixture (2.33% w/w), a 12:9:3 ethoxydiglycol:PG:PG monocaprylate solvent mixture (2.43% w/w), and a 12:12:0 ethoxydiglycol:PG:PG monocaprylate solvent mixture (2.20% w/w) were all higher than in PG alone (i.e. 1.30% w/w) (see Table 2).

Addition of ethoxydiglycol to PG alone (i.e. a 12:12:0 ethoxydiglycol:PG:PG monocaprylate solvent mixture) increased the solubility of hydrocortisone 1.7-fold over its solubility in PG alone (2.20% w/w compared to 1.30% w/w). Addition of ethoxydiglycol to PG monocaprylate alone (i.e. a 12:0:12 ethoxydiglycol:PG:PG monocaprylate solvent mixture) also increased the solubility of hydrocortisone 2.3-fold over its solubility in PG monocaprylate alone (1.25% w/w compared to 0.55% w/w).

The results suggest a synergistic effect between ethoxydiglycol and each of PG, PG monocaprylate, and a PG:PG monocaprylate mixture. Specifically, the results demonstrate the increased solubility of hydrocortisone in a combination of ethoxydiglycol and PG; ethoxydiglycol and PG monocaprylate; and ethoxydiglycol and a PG:PG monocaprylate mixture over the solubility of hydrocortisone in each of PG, PG monocaprylate, and a PG:PG monocaprylate mixture alone, respectively.

Example 3—Solubility of Hydrocortisone in Mixtures of Components

The solubility of hydrocortisone in mixtures of PG and PG monolaurate was measured according to the procedure in Example 1.

Solubility (% w/w) results are presented in Table 4 and FIG. 2.

TABLE 4

| PG:PG Monolaurate | Solubility (% w/w) |
| --- | --- |
| 100:0 | 1.30 |
| 75:25 | 1.75 |
| 50:50 | 1.40 |
| 25:75 | 0.80 |
| 0:100 | 0.30 |

In FIG. 2, the vertical axes indicate solubility (% w/w). The horizontal axis indicates the PG:PG monolaurate ratio in a given solvent mixture. The dashed solubility line indicates the expected solubility if each solvent (PG and PG monolaurate) acted independently in a solvent mixture. The upper line (◆) depicts actual results of hydrocortisone solubility in a PG:PG monolaurate solvent mixture.

FIG. 2 demonstrates that for each tested solvent mixture that contained both solvents (◆), hydrocortisone was more soluble in the mixture than expected (dashed line).

Solubility of hydrocortisone in a 50:50 PG:PG monolaurate solvent mixture (1.40% w/w) and a 75:25 PG:PG monolaurate solvent mixture (1.75% w/w) were each higher than in PG alone (i.e. 100:0 solvent mixture; 1.30% w/w). These results suggest a synergistic effect between PG and PG monolaurate.

Example 4—Solubility of Hydrocortisone in Mixtures of Components

The solubility of hydrocortisone in mixtures of ethoxydiglycol and PG monocaprylate was measured according to the procedure in Example 1.

Figure 3:
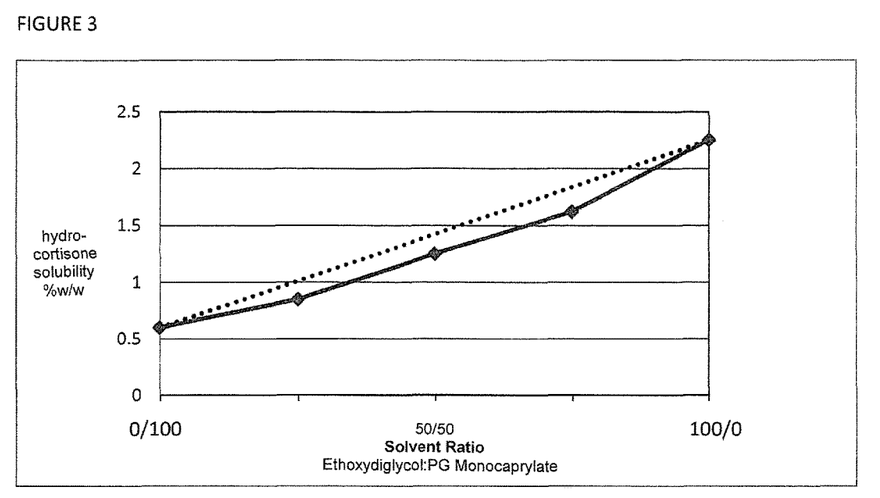
FIG. 3 depicts the solubility of hydrocortisone in mixtures of ethoxydiglycol and propylene glycol monocaprylate.

Solubility (% w/w) results are presented in Table 5 and FIG. 3.

TABLE 5

| Ethoxydiglycol:PG Monocaprylate | Solubility (% w/w) |
| --- | --- |
| 100:0 | 2.25 |
| 90:10 | 2.00 |
| 75:25 | 1.62 |
| 50:50 | 1.25 |
| 25:75 | 0.85 |
| 0:100 | 0.55 |

In FIG. 3, the vertical axes indicate solubility (% w/w). The horizontal axis indicates the ethoxydiglycol:PG monocaprylate ratio in a given solvent mixture. The dashed solubility line indicates the expected solubility if each solvent (ethoxydiglycol and PG monocaprylate) acted independently in a solvent mixture. The lower line depicts actual results of hydrocortisone solubility in a ethoxydiglycol:PG monocaprylate solvent mixture.

FIG. 3 demonstrates that for each tested solvent mixture that contained both solvents (lower line), hydrocortisone was less soluble in the mixture than expected (dashed line). These results suggest a diluting or interfering effect between ethoxydiglycol and PG monocaprylate.

Example 5—Solubility of Triamcinolone Acetonide in Mixtures of Components

A) Mixtures of PG and PG Monocaprylate

The solubility of triamcinolone acetonide in mixtures of PG and PG monocaprylate was measured according to the procedure in Example 1.

Figure 4:
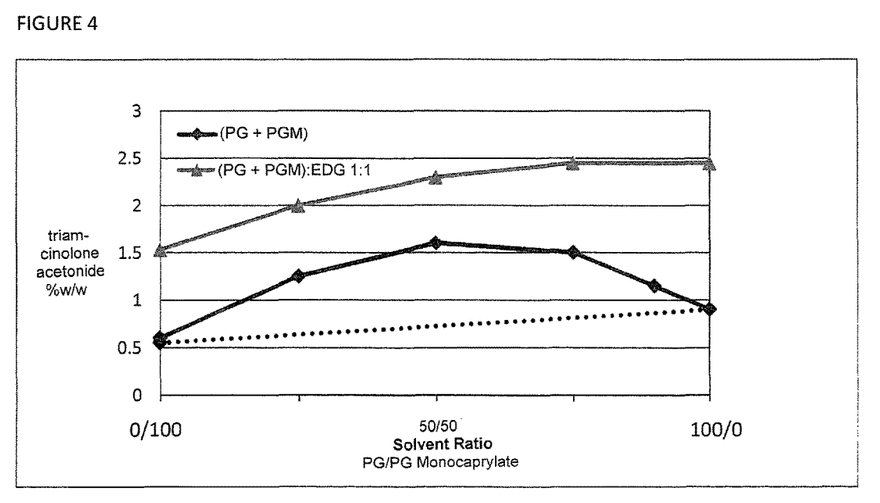
FIG. 4 depicts the solubility of triamcinolone acetonide in mixtures of propylene glycol and propylene glycol monocaprylate, or of propylene glycol, propylene glycol monocaprylate, and ethoxydiglycol.

Solubility (% w/w) results are presented in Table 6 and FIG. 4.

TABLE 6

| PG:PG Monocaprylate | Solubility (% w/w) |
| --- | --- |
| 100:0 | 0.90 |
| 90:10 | 1.15 |
| 75:25 | 1.50 |
| 50:50 | 1.60 |

TABLE 6-continued

| PG:PG Monocaprylate | Solubility (% w/w) |
| --- | --- |
| 25:75 | 1.25 |
| 0:100 | 0.60 |

In FIG. 4, the vertical axes indicate solubility (% w/w). The horizontal axis indicates the PG:PG monocaprylate ratio (w:w) in a given solvent mixture. The dashed solubility line indicates the expected solubility if each solvent (PG and PG monocaprylate) acted independently in a solvent mixture. The middle line (◆) depicts actual results of triamcinolone acetonide solubility in a PG:PG monocaprylate solvent mixture. The upper line (▲) depicts actual results of triamcinolone acetonide solubility in an ethoxydigycol:PG:PG monocaprylate solvent mixture.

FIG. 4 demonstrates that for each tested solvent mixture that contained both PG and PG monocaprylate (◆), triamcinolone acetonide was more soluble in the mixture than expected (dashed line).

Solubility of triamcinolone acetonide in a 25:75 PG:PG monocaprylate solvent mixture (1.25% w/w), a 50:50 PG:PG monocaprylate solvent mixture (1.60% w/w), a 75:25 PG:PG monocaprylate solvent mixture (1.50% w/w), and a 90:10 PG:PG monocaprylate solvent mixture (1.15% w/w) were all higher than in PG alone (i.e. 100:0 solvent mixture; 0.90% w/w). These results suggest a synergistic effect between PG and PG monocaprylate.

B) Effect of Addition of Ethoxydiglycol on Triamcinolone Acetonide Solubility in Mixtures of PG and PG Monocaprylate The solubility of triamcinolone acetonide in mixtures of PG, PG monocaprylate, and ethoxydiglycol was measured according to the procedure in Example 1.

Solubility (% w/w) results are presented in Table 7 and FIG. 4.

TABLE 7

| Ethoxydiglycol:PG:PG Monocaprylate | Solubility (% w/w) |
| --- | --- |
| 12:12:0 | 2.45 |
| 12:9:3 | 2.45 |
| 12:6:6 | 2.30 |
| 12:3:9 | 2.00 |
| 12:0:12 | 1.53 |

FIG. 4 demonstrates that triamcinolone acetonide was more soluble in a ethoxydiglycol:PG:PG monocaprylate solvent mixture (▲) than in a PG:PG monocaprylate solvent mixture (◆).

Solubility of triamcinolone acetonide in a 12:3:9 ethoxydiglycol:PG:PG monocaprylate solvent mixture (2.00% w/w), a 12:6:6 ethoxydiglycol:PG:PG monocaprylate solvent mixture (2.30% w/w), a 12:9:3 ethoxydiglycol:PG:PG monocaprylate solvent mixture (2.45% w/w), and a 12:12:0 ethoxydiglycol:PG:PG monocaprylate solvent mixture (2.45% w/w) were all higher than in PG alone (i.e. 0.90% w/w) (see Table 6).

Addition of ethoxydiglycol to PG alone (i.e. a 12:12:0 ethoxydiglycol:PG:PG monocaprylate solvent mixture) increased the solubility of triamcinolone acetonide 1.7-fold over its solubility in PG alone (2.45% w/w compared to 0.90% w/w). Addition of ethoxydiglycol to PG monocaprylate alone (i.e. a 12:0:12 ethoxydiglycol:PG:PG monocaprylate solvent mixture) also increased the solubility of hydrocortisone 2.3-fold over its solubility in PG monocaprylate alone (1.53% w/w compared to 0.60% w/w).

The results suggest a synergistic effect between ethoxydiglycol and each of PG, PG monocaprylate, and a PG:PG monocaprylate mixture. Specifically, the results demonstrate the increased solubility of triamcinolone acetonide in a combination of ethoxydiglycol and PG; ethoxydiglycol and PG monocaprylate; and ethoxydiglycol and a PG:PG monocaprylate mixture over the solubility of hydrocortisone in each of PG, PG monocaprylate, and a PG:PG monocaprylate mixture alone, respectively.

Example 6—Effect of Water on Corticosteroid Solubility

The solubility of hydrocortisone in various solvents, each with and without the addition of water, was measured according to the procedure in Example 1.

Solubility (% w/w) results are presented in Table 8.

TABLE 8

| Solvent Mixture (% w/w) | Solubility (% w/w) |
|---|---|
| Ethoxydiglycol:Purified Water 100:0 | 2.25 |
| Ethoxydiglycol:Purified Water 90:10 | 3.65 |
| PG Monocaprylate:Purified Water 100:0 | 0.55 |
| PG Monocaprylate:Purified Water 95:5 | 1.32 |
| Ethoxydiglycol:PG Caprylate:PG 12:8:4 | 1.90 |
| Ethoxydiglycol:PG Caprylate:PG (12:8:4):Purified Water 90:10 | 2.85 |

Results demonstrate that hydrocortisone was more soluble in a given solvent with water than the same solvent without water. Hydrocortisone was 1.6 times more soluble in ethoxydiglycol with water than without. Hydrocortisone was 2.4 times more soluble in propylene glycol monocaprylate with water than without. Hydrocortisone was 1.5 times more soluble in an ethoxydiglycol, propylene glycol monocaprylate, and propylene glycol solvent mixture with water than without.

The results suggest a synergistic effect between water and each of ethoxydiglycol, PG monocaprylate, and an ethoxydiglycol:PG monocaprylate:PG mixture. Specifically, the results demonstrate the increased solubility of hydrocortisone in a combination of water and ethoxydiglycol; water and PG monocaprylate; and water and an ethoxydiglycol:PG monocaprylate:PG mixture over the solubility of hydrocortisone in each of ethoxydiglycol, PG monocaprylate, and an ethoxydiglycol:PG monocaprylate:PG mixture alone, respectively.

Example 7—Hydrocortisone Topical Cream Formulations

A topical formulation is prepared as a cream comprising the corticosteroid hydrocortisone, the fatty acid ester propylene glycol monocaprylate, and the pharmaceutically acceptable solvents propylene glycol and diethylene glycol monoethyl ether. Components (w/w %) of various formulations of hydrocortisone 1% (Formulations A and B) and 2.5% (Formulations C and D) creams are presented in Table 9.

TABLE 9

| Ingredient | A | B | C | D |
|---|---|---|---|---|
| Hydrocortisone | 1.0 | 1.0 | 2.5 | 2.5 |
| Lactic Acid | 12.0 | 12.0 | 12.0 | 12.0 |

TABLE 9-continued

| Ingredient | A | B | C | D |
|---|---|---|---|---|
| Stearyl Alcohol | 8.8 | 8.8 | 8.0 | 6.0 |
| Cetyl Alcohol | 2.3 | 2.3 | 2.0 | 2.0 |
| Propylene Glycol Monocaprylate | 8.0 | 6.0 | 8.0 | 8.0 |
| Steareth-2 | 2.0 | 2.0 | 2.0 | — |
| Steareth-21 | 2.0 | 2.0 | 2.0 | — |
| Sorbitan Monostearate | — | — | — | 2.0 |
| PEG-40 Stearate | — | — | — | 2.0 |
| Propylene Glycol | 4.0 | 6.0 | 3.0 | 4.0 |
| Diethylene Glycol Monoethyl Ether | 10.0 | 6.0 | 9.0 | 10.0 |
| Methylparaben | 0.12 | 0.12 | 0.12 | 0.12 |
| Propylparaben | 0.03 | 0.03 | 0.03 | 0.03 |
| Sodium Hydroxide | 3.1 | 3.1 | 3.1 | 3.1 |
| Purified Water | qs 100 | qs 100 | qs 100 | qs 100 |

Example 8—Hydrocortisone Acetate Topical Cream Formulations

A topical formulation is prepared as a cream comprising the corticosteroid hydrocortisone acetate, the fatty acid ester propylene glycol monocaprylate, and the pharmaceutically acceptable solvents propylene glycol, hexylene glycol, and diethylene glycol monoethyl ether. Components (w/w %) of various formulations of hydrocortisone acetate 1% (Formulations A) and 2.5% (Formulations B, C, and D) creams are presented in Table 10.

TABLE 10

| Ingredient | A | B | C | D |
|---|---|---|---|---|
| Hydrocortisone Acetate | 1.0 | 2.5 | 2.5 | 2.5 |
| Lactic Acid | 12.0 | 12.0 | 12.0 | 12.0 |
| Stearyl Alcohol | 9.0 | 9.0 | 8.0 | 8.0 |
| Cetyl Alcohol | 2.5 | 2.0 | 2.0 | 2.5 |
| Propylene Glycol Monocaprylate | 8.0 | 8.0 | 6.0 | 6.0 |
| Steareth-2 | 2.0 | 2.0 | 1.5 | 2.0 |
| Steareth-21 | 2.0 | 2.0 | 1.5 | 2.0 |
| Propylene Glycol | 4.0 | 4.0 | 2.0 | — |
| Hexylene Glycol | — | — | — | 2.0 |
| Diethylene Glycol Monoethyl Ether | 8.0 | 8.0 | 6.0 | 6.0 |
| Methylparaben | 0.12 | 0.12 | 0.12 | 0.12 |
| Propylparaben | 0.03 | 0.03 | 0.03 | 0.03 |
| Sodium Hydroxide | 3.1 | 3.1 | 3.1 | 3.1 |
| Purified Water | qs 100 | qs 100 | qs 100 | qs 100 |

Example 9—Hydrocortisone Acetate Topical Oil-in-Water Emulsion Formulations

A topical formulation is prepared as an oil-in-water emulsion comprising the corticosteroid hydrocortisone acetate, the fatty acid esters propylene glycol monocaprylate or propylene glycol monolaurate, and the pharmaceutically acceptable solvents propylene glycol, and diethylene glycol monoethyl ether. Components (w/w %) of various formulations of hydrocortisone acetate 1% (Formulations A) and 2.5% (Formulations B, C, and D) emulsions are presented in Table 11.

TABLE 11

| Ingredient | A | B | C | D |
|---|---|---|---|---|
| Hydrocortisone Acetate | 1.0 | 2.5 | 2.5 | 2.5 |
| Stearyl Alcohol | 8.0 | 9.0 | 9.0 | 9.0 |
| Cetyl Alcohol | 2.0 | 2.0 | 3.0 | 3.0 |
| Propylene Glycol Monocaprylate | 6.0 | 8.0 | 6.0 | — |

TABLE 11-continued

| Ingredient | A | B | C | D |
|---|---|---|---|---|
| Propylene Glycol Monolaurate | — | — | — | 6.0 |
| Steareth-2 | 1.5 | 2.0 | — | 2.0 |
| Steareth-21 | 1.5 | 1.0 | — | 2.0 |
| PEG-100 Stearate | — | — | 1.5 | — |
| Sorbitan Monostearate | — | — | 1.5 | — |
| Propylene Glycol | 3.0 | 4.0 | 3.0 | 3.0 |
| Diethylene Glycol Monoethyl Ether | 6.0 | 8.0 | 6.0 | 6.0 |
| Methylparaben | 0.12 | 0.12 | 0.12 | 0.12 |
| Propylparaben | 0.03 | 0.03 | 0.03 | 0.03 |
| Purified Water | qs 100 | qs 100 | qs 100 | qs 100 |

Example 10—Hydrocortisone Acetate Topical Oil-in-Water Emulsion Formulations

A topical formulation is prepared as a gel or lotion comprising the corticosteroid hydrocortisone acetate, the fatty acid esters propylene glycol monocaprylate or propylene glycol monolaurate, and the pharmaceutically acceptable solvents propylene glycol, and diethylene glycol monoethyl ether. Components (w/w %) of various formulations of hydrocortisone acetate 1% (Formulations A) and 2.5% (Formulations B and C) gels or lotions are presented in Table 12.

TABLE 12

| Ingredient | A | B | C |
|---|---|---|---|
| Hydrocortisone Acetate | 1.0 | 2.5 | 2.5 |
| Cetostearyl Alcohol | — | 3.0 | 3.0 |
| Propylene Glycol Monocaprylate | 5.0 | 8.0 | — |
| Propylene Glycol Monolaurate | — | — | 6.0 |
| Carbomer Homopolymer Type B | 0.5 | 0.5 | 0.5 |
| Carbomer Copolymer Type A | 0.2 | 0.2 | 0.2 |
| PEG-100 Stearate | 0.3 | 0.3 | 0.3 |
| Propylene Glycol | 3.0 | 4.0 | 3.0 |
| Diethylene Glycol Monoethyl Ether | 5.0 | 8.0 | 10.0 |
| Methylparaben | 0.12 | 0.12 | 0.12 |
| Propylparaben | 0.03 | 0.03 | 0.03 |
| Sodium Hydroxide | 0.1 | 0.1 | 0.1 |
| Purified Water | qs 100 | qs 100 | qs 100 |

Example 11—Clobetasol Propionate Topical Cream Formulations

A topical formulation is prepared as a cream comprising the corticosteroid clobetasol propionate, the fatty acid esters propylene glycol monocaprylate or propylene glycol monolaurate, and the pharmaceutically acceptable solvent propylene glycol with or without diethylene glycol monoethyl ether. Components (w/w %) of various formulations (A and B) of clobetasol propionate creams are presented in Table 13.

TABLE 13

| Ingredient | A | B |
|---|---|---|
| Clobetasol Propionate | 0.05 | 0.05 |
| Lactic Acid | 12.0 | — |
| Stearyl Alcohol | 6.0 | 8.0 |
| Cetyl Alcohol | 1.5 | 2.0 |
| Propylene Glycol Monocaprylate | 3.0 | — |
| Propylene Glycol Monolaurate | — | 5.0 |
| Steareth-2 | 2.0 | — |
| Steareth-21 | 2.0 | — |
| Carbomer Copolymer Type A | — | 0.2 |
| PEG-40 Stearate | — | 1.0 |
| Propylene Glycol | 4.0 | 10.0 |
| Diethylene Glycol Monoethyl Ether | 12.0 | — |
| Methylparaben | 0.12 | 0.12 |
| Propylparaben | 0.03 | 0.03 |
| Sodium Hydroxide | 3.1 | 0.1 |
| Purified Water | qs 100 | qs 100 |

Example 12—Betamethasone Dipropionate Topical Cream Formulations

A topical formulation is prepared as a cream comprising the corticosteroid betamethasone dipropionate, the fatty acid esters propylene glycol monocaprylate or propylene glycol monolaurate, and the pharmaceutically acceptable solvent propylene glycol with or without diethylene glycol monoethyl ether. Components (w/w %) of various formulations (A and B) of betamethasone dipropionate creams are presented in Table 14.

TABLE 14

| Ingredient | A | B |
|---|---|---|
| Betamethasone Dipropionate | 0.05 | 0.05 |
| Lactic Acid | 12.0 | — |
| Stearyl Alcohol | 6.0 | 8.0 |
| Cetyl Alcohol | 1.5 | 2.0 |
| Propylene Glycol Monocaprylate | 3.0 | — |
| Propylene Glycol Monolaurate | — | 5.0 |
| Steareth-2 | 2.0 | — |
| Steareth-21 | 2.0 | — |
| Carbomer Copolymer Type A | — | 0.2 |
| PEG-40 Stearate | — | 1.0 |
| Propylene Glycol | 3.0 | 10.0 |
| Diethylene Glycol Monoethyl Ether | 9.0 | — |
| Methylparaben | 0.12 | 0.12 |
| Propylparaben | 0.03 | 0.03 |
| Sodium Hydroxide | 3.1 | 0.1 |
| Purified Water | qs 100 | qs 100 |

Example 13—Triamcinolone Acetonide Topical Cream Formulations

A topical formulation is prepared as a cream comprising the corticosteroid triamcinolone acetonide, the fatty acid esters propylene glycol monocaprylate or propylene glycol monolaurate, and the pharmaceutically acceptable solvents propylene glycol and diethylene glycol monoethyl ether. Components (w/w %) of various formulations (A and B) of triamcinolone acetonide creams are presented in Table 15.

TABLE 15

| Ingredient | A | B | C |
|---|---|---|---|
| Triamcinolone Acetonide | 0.1 | 0.5 | 0.1 |
| Lactic Acid | 12.0 | — | — |
| Stearyl Alcohol | 8.0 | 8.0 | 8.0 |
| Cetyl Alcohol | 2.0 | 2.0 | 2.0 |
| Propylene Glycol Monocaprylate | 4.0 | 8.0 | — |
| Propylene Glycol Monolaurate | — | — | 6.0 |
| Steareth-2 | 2.0 | — | — |
| Steareth-21 | 2.0 | — | — |
| Carbomer Copolymer Type A | — | 0.2 | 0.2 |
| PEG-40 Stearate | — | 1.0 | 1.0 |
| Propylene Glycol | 4.0 | 6.0 | 6.0 |
| Diethylene Glycol Monoethyl Ether | 8.0 | 6.0 | — |
| Methylparaben | 0.12 | 0.12 | 0.12 |

TABLE 15-continued

| Ingredient | A | B | C |
|---|---|---|---|
| Propylparaben | 0.03 | 0.03 | 0.03 |
| Sodium Hydroxide | 3.1 | 0.05 | 0.05 |
| Purified Water | qs 100 | qs 100 | qs 100 |

Example 14—Clobetasol Propionate Topical Gel and Lotion Formulations

A topical formulation is prepared as a gel or lotion comprising the corticosteroid clobetasol propionate, the fatty acid ester propylene glycol monocaprylate, and the pharmaceutically acceptable solvent propylene glycol with or without diethylene glycol monoethyl ether. Components (w/w %) of various formulations (A and B) of clobetasol propionate gels or lotions are presented in Table 16.

TABLE 16

| Ingredient | A | B |
|---|---|---|
| Clobetasol Propionate | 0.05 | 0.05 |
| Cetostearyl Alcohol | — | 3.0 |
| Propylene Glycol Monocaprylate | 5.0 | 3.0 |
| Carbomer Copolymer Type A | 0.2 | 0.2 |
| Carbomer Homopolymer Type C | 0.5 | 0.5 |
| PEG-40 Stearate | 0.5 | 0.5 |
| Propylene Glycol | 5.0 | 10.0 |
| Diethylene Glycol Monoethyl Ether | 5.0 | — |
| Methylparaben | 0.12 | 0.12 |
| Propylparaben | 0.03 | 0.03 |
| Sodium Hydroxide | 0.1 | 0.1 |
| Purified Water | qs 100 | qs 100 |

Example 15—Betamethasone Dipropionate Topical Gel and Lotion Formulations

A topical formulation is prepared as a gel or lotion comprising the corticosteroid betamethasone dipropionate, the fatty acid ester propylene glycol monolaurate, and the pharmaceutically acceptable solvent propylene glycol with or without diethylene glycol monoethyl ether. Components (w/w %) of various formulations (A and B) of betamethasone dipropionate gels or lotions are presented in Table 17.

TABLE 17

| Ingredient | A | B |
|---|---|---|
| Betamethasone Dipropionate | 0.05 | 0.05 |
| Cetostearyl Alcohol | — | 3.0 |
| Propylene Glycol Monolaurate | 5.0 | 3.0 |
| Carbomer Copolymer Type A | 0.2 | 0.2 |
| Carbomer Homopolymer Type C | 0.5 | 0.5 |
| PEG-40 Stearate | 0.5 | 0.5 |
| Propylene Glycol | 5.0 | 10.0 |
| Diethylene Glycol Monoethyl Ether | 5.0 | — |
| Methylparaben | 0.12 | 0.12 |
| Propylparaben | 0.03 | 0.03 |
| Sodium Hydroxide | 0.1 | 0.1 |
| Purified Water | qs 100 | qs 100 |

Example 16—Hydrocortisone Topical Ointment Formulations

A topical formulation is prepared as an ointment comprising the corticosteroid hydrocortisone, the fatty acid ester propylene glycol monocaprylate, and the pharmaceutically acceptable solvents propylene glycol and diethylene glycol monoethyl ether. Components (w/w %) of various formulations (A and B) of hydrocortisone ointments are presented in Table 18.

TABLE 18

| Ingredient | A | B |
|---|---|---|
| Hydrocortisone | 1.0 | 2.5 |
| Stearyl Alcohol | 10.0 | 12.0 |
| Polyethylene Glycol 400 | 51.0 | 40.5 |
| Methoxy-PEG 350 | — | 10.0 |
| Propylene Glycol Monocaprylate | 10.0 | 12.0 |
| Sorbitan Monostearate | 3.0 | 3.0 |
| Propylene Glycol | 20.0 | 10.0 |
| Diethylene Glycol Monoethyl Ether | 5.0 | 10.0 |

Example 17—Betamethasone Dipropionate Topical Ointment Formulations

A topical formulation is prepared as an ointment comprising the corticosteroid betamethasone dipropionate, the fatty acid ester propylene glycol monolaurate or propylene glycol monocaprylate, and the pharmaceutically acceptable solvents propylene glycol and diethylene glycol monoethyl ether. Components (w/w %) of various formulations (A and B) of betamethasone dipropionate ointments are presented in Table 19.

TABLE 19

| Ingredient | A | B |
|---|---|---|
| Betamethasone Dipropionate | 0.05 | 0.05 |
| Stearyl Alcohol | 10.0 | 8.0 |
| Polyethylene Glycol 400 | 62.95 | 53.95 |
| Methoxy-PEG 350 | — | 10.0 |
| Propylene Glycol Monolaurate | — | 5.0 |
| Propylene Glycol Monocaprylate | 4.0 | — |
| Sorbitan Monostearate | 3.0 | 3.0 |
| Propylene Glycol | 15.0 | 10.0 |
| Diethylene Glycol Monoethyl Ether | 5.0 | 10.0 |

The above specification and examples provide a complete description of fatty acid esters as steroid solvents. Although various embodiments have been described above with a certain degree of particularity, or with reference to one or more individual embodiments, those skilled in the art could make numerous alterations to the disclosed embodiments without departing from the spirit or scope of this disclosure. Other embodiments are therefore contemplated. All matter contained in the above description is illustrative only of particular embodiments and not limiting. Changes in detail or structure can be made without departing from the basic elements described herein. For instance, various combinations of components, amounts, and ratios, and selection of individual components, amounts, and ratios from those listed and embodied are within the scope of the disclosure, including individual selections, selections of two in combination, selections of three in combination, etc. from within those listed and embodied.

What is claimed is:
1. A pharmaceutical composition comprising:
   a mixture of solvent components, comprising propylene glycol monocaprylate and propylene glycol in a ratio from 90:10 to 25:75; and
   a corticosteroid selected from hydrocortisone or hydrocortisone acetate at 1.0% w/w to 5.0% w/w of the pharmaceutical composition, wherein the corticosteroid is dissolved in the solvent mixture at 1.25% w/w to 1.70% w/w of the solvent mixture;

wherein the pharmaceutical composition is a topical formulation selected from a cream, gel, and ointment.

2. The pharmaceutical composition of claim 1, wherein the corticosteroid is at 1.25% w/w to 5.0% w/w of the pharmaceutical composition.

3. The pharmaceutical composition of claim 1, further comprising at least one humectant selected from ethylene glycol, fructose, glycerol, lactic acid, polyethylene glycol, sorbitan, sorbitol, tetraethylene glycol, triethylene glycol, and vitamin B.

4. The pharmaceutical composition of claim 3, wherein the humectant is lactic acid.

5. The pharmaceutical composition of claim 1, wherein the corticosteroid is at 1.50% w/w to 5.0% w/w of the pharmaceutical composition.

6. The pharmaceutical composition of claim 1, wherein the corticosteroid is at 1.65% w/w to 5.0% w/w of the pharmaceutical composition.

7. The pharmaceutical composition of claim 1, wherein the corticosteroid is at 1.0% w/w to 3.0% w/w of the pharmaceutical composition.

8. The pharmaceutical composition of claim 1, wherein the concentration of the corticosteroid dissolved in the solvent mixture is from 1.50% w/w to 1.70% w/w of the solvent mixture.

9. The pharmaceutical composition of claim 1, wherein the concentration of the corticosteroid dissolved in the solvent mixture is from 1.65 w/w to 1.70% w/w of the solvent mixture.

10. The pharmaceutical composition of claim 1, wherein the corticosteroid is at 2.5% w/w to 5.0 w/w of the pharmaceutical composition.

11. The pharmaceutical composition of claim 1, wherein the corticosteroid is at 2.5% w/w to 3.0% w/w of the pharmaceutical composition.

12. The pharmaceutical composition of claim 1, wherein the corticosteroid is at 2.5% w/w of the pharmaceutical composition.

13. The pharmaceutical composition of claim 1, wherein the formulation is a cream comprising an oil phase, a water phase and an emulsifier.

14. The pharmaceutical composition of claim 1, wherein the formulation is a gel comprising a gelling agent selected from the group consisting of starch, cellulose derivatives, carbomers, magnesium-aluminum silicates, xanthan gum, colloidal silica, and aluminum or zinc soaps.

15. The pharmaceutical composition of claim 1, wherein the formulation is an ointment comprising greater than 50% by weight hydrocarbons, waxes, or polyethylene glycol.

16. A pharmaceutical composition comprising:
a mixture of solvent components, comprising propylene glycol monocaprylate, propylene glycol and ethoxydiglycol, wherein the propylene glycol monocaprylate and propylene glycol are in a ratio from 90:10 to 25:75; and
a corticosteroid selected from hydrocortisone or hydrocortisone acetate at 1.0% w/w to 5.0% w/w of the pharmaceutical composition, wherein the corticosteroid is dissolved in the solvent mixture at 1.90% w/w to 2.43% w/w of the solvent mixture;
wherein the pharmaceutical composition is a topical formulation selected from a cream, gel, and ointment.

17. The pharmaceutical composition of claim 16, wherein the ratio of ethoxydiglycol to the total of propylene glycol monocaprylate and propylene glycol is 1:1.

18. The pharmaceutical composition of claim 16, wherein the corticosteroid is at 2.5% w/w to 5.0% w/w of the pharmaceutical composition.

19. The pharmaceutical composition of claim 16, wherein the corticosteroid is at 2.5% w/w to 3.0% w/w of the pharmaceutical composition.

20. The pharmaceutical composition of claim 16, wherein the concentration of the corticosteroid dissolved in the solvent mixture is from 2.17% w/w to 2.43% w/w of the solvent mixture.

21. The pharmaceutical composition of claim 16, wherein the concentration of the corticosteroid dissolved in the solvent mixture is from 2.33% w/w to 2.43% w/w of the solvent mixture.

22. The pharmaceutical composition of claim 16, wherein the corticosteroid is at 2.5% w/w of the pharmaceutical composition.

* * * * *

UNITED STATES PATENT AND TRADEMARK OFFICE
CERTIFICATE OF CORRECTION

PATENT NO. : 10,111,956 B2
APPLICATION NO. : 14/294764
DATED : October 30, 2018
INVENTOR(S) : Robert Lathrop and David Wade Osborne Page 1 of 1

It is certified that error appears in the above-identified patent and that said Letters Patent is hereby corrected as shown below:

In the Claims

In Column 26, Claim 1, Lines 63-65, please delete "comprising propylene glycol monocaprylate and propylene glycol in a ratio from 90:10 to 25:75" and insert --comprising propylene glycol and propylene glycol monocaprylate in a ratio from 90:10 to 25:75--

In Column 28, Claim 16, Lines 12-13, please delete "wherein the propylene glycol monocaprylate and propylene glycol are in a ratio from 90:10 to 25:75; and" and insert --wherein the propylene glycol and propylene glycol monocaprylate are in a ratio from 90:10 to 25:75;--

Signed and Sealed this
Fifth Day of February, 2019

Andrei Iancu
*Director of the United States Patent and Trademark Office*